United States Patent [19]
Ducker et al.

[11] Patent Number: 5,944,705
[45] Date of Patent: Aug. 31, 1999

[54] ABSORBENT ARTICLES WITH IMPROVED RASH-PREVENTING PROPERTIES

[75] Inventors: Paul M. Ducker, Vancouver; Richard S. Dietel, Amboy; Gary Nicklett, Brush Prairie, all of Wash.

[73] Assignee: Drypers Corporation, Houston, Tex.

[21] Appl. No.: 08/923,195

[22] Filed: Sep. 4, 1997

Related U.S. Application Data

[63] Continuation-in-part of application No. 08/853,267, May 9, 1997.

[51] Int. Cl.⁶ ..................................................... A61F 13/15
[52] U.S. Cl. .......................... 604/364; 604/358; 604/360; 604/363
[58] Field of Search ................................... 604/360, 358; 424/402; 427/180

[56] References Cited

U.S. PATENT DOCUMENTS

| | | |
|---|---|---|
| 3,896,807 | 7/1975 | Buchalter . |
| 4,556,560 | 12/1985 | Buckingham . |
| 4,711,780 | 12/1987 | Fahim . |
| 4,732,797 | 3/1988 | Johnson et al. . |
| 4,772,501 | 9/1988 | Johnson et al. . |
| 4,882,204 | 11/1989 | Tenenbaum ............................ 427/180 |
| 4,959,059 | 9/1990 | Eilender et al. . |
| 4,996,238 | 2/1991 | Matravers . |
| 5,043,155 | 8/1991 | Puchalski et al. . |
| 5,049,440 | 9/1991 | Bornhoeft, III et al. . |
| 5,141,803 | 8/1992 | Pregozen . |
| 5,332,118 | 7/1994 | Muckenfuhs . |
| 5,362,488 | 11/1994 | Sibley et al. . |
| 5,436,007 | 7/1995 | Hartung et al. .......................... 424/402 |
| 5,525,346 | 6/1996 | Hartung et al. .......................... 424/402 |
| 5,607,760 | 3/1997 | Roe . |
| 5,609,587 | 3/1997 | Roe ........................................ 604/360 |
| 5,624,676 | 4/1997 | Mackey et al. . |
| 5,635,191 | 6/1997 | Roe et al. . |
| 5,643,588 | 7/1997 | Roe et al. ............................... 424/402 |
| 5,648,083 | 7/1997 | Blieszner et al. . |

*Primary Examiner*—John G. Weiss
*Assistant Examiner*—Miley Craig Peppers
*Attorney, Agent, or Firm*—Fulbright & Jaworski L.L.P.

[57] ABSTRACT

An absorbent article, such as a disposable diaper, disposable training pants, feminine hygiene products or an incontinent adult article, containing aloe vera on at least the surface of the article contacting the wearer's skin to reduce rash and methods of making same.

43 Claims, No Drawings

ABSORBENT ARTICLES WITH IMPROVED RASH-PREVENTING PROPERTIES

CROSS REFERENCE TO RELATED APPLICATION

This application is a continuation-in-part of application Ser. No. 08/853,267, filed May 9, 1997, entitled "Absorbent Articles with Improved Rash-Preventing Properties".

BACKGROUND OF INVENTION

The present invention relates to absorbent articles having improved rash-preventing properties and, particularly, to disposable diapers, disposable training pants, feminine hygiene products and adult incontinence products and methods of making same that include aloe vera gel and aloe vera solutions to reduce the occurrence of rashes often associated with such products.

Absorbent articles, such as disposable diapers, disposable training pants, feminine hygiene products and adult incontinence products, are becoming increasingly common. These articles strive to effectively absorb bodily discharge, such as urine, while keeping the wearer's skin as dry as possible. While current absorbent articles exhibit increasingly improving absorbency properties, wearers continue to periodically experience rash, generally understood to result from contact between certain portions of a wearer's body, oftentimes the buttocks and crotch areas, and areas of the articles that contain or have been exposed to discharge or areas of the article of relatively high pressure. For reference purposes, the following discussion refers to such rashes by the commonly used phrase "diaper rash," with the understanding that the phrase refers to any such rash, irrespective of the type of absorbent article in question.

A variety of creams, powders, lotions and ointments have been proposed to prevent or reduce rash by creating a barrier layer to protect the exposed body areas from the rash-inducing discharge or high pressure. Such compositions generally attempt to alleviate diaper rash or prevent diaper rash or both. Examples of such products are disclosed by U.S. Pat. No. 4,556,560 and No. 4,996,238. One such lubricant is petrolatum. For example, U.S. Pat. No. 3,896,807 discloses the addition of petrolatum to the top sheet of a diaper in an attempt to reduce diaper rash irritation.

In addition to the above lubricants, ointments and the like, aloe vera has been recognized as a material that may be useful in treating or preventing diaper rash. For example, U.S. Pat. No. 5,362,488; No. 5,436,007 and No. 4,711,780 describe various creams and lotions that include aloe vera or aloe vera derivatives and are used to treat diaper rash. In addition, U.S. Pat. No. 5,043,155; No. 5,332,118; No. 4,732,797; No. 4,772,501; No. 5,049,440 and No. 5,141,803 describe baby wipes that include aloe vera, for example, as a moisturizer.

Aloe vera also has been included in disposable absorbent articles. For example, U.S. Pat. No. 4,959,059 describes an ambulatory adult pad for reducing bedsores, pressure sores, decubitus ulcers and similar lesions. In one embodiment, the pad may include 15–25 grams per square meter of aloe vera as a free lubricant layer. U.S. Pat. No. 5,525,346 describes a diaper rash lotion that may include 0–5% by weight of aloe vera. In one embodiment, the lotion, which is an oil-in-water emulsion that includes a buffering system of citric acid and sodium citrate, is impregnated into the diaper. Also, U.S. Pat. No. 4,882,204, is directed to a method for spraying baby powder onto and into diapers to increase the absorbency of the diapers. The patent mentions that from about 0.3–4.5% by weight of Alocel C, an aloe vera extract, may be included in the powder as a skin protectant.

The articles, creams and methods disclosed in the aforementioned patents are somewhat useful in alleviating rashes. These articles, however, fail to disclose an article with effective concentrations of preferred compositions, such as aloe vera, that can be produced by a simple method. Furthermore, the references which disclose aloe vera fail to adequately reduce friction between the wearer's skin and high pressure areas of the articles and methods of making the same. Additionally, the references fail to address processing and spoilage considerations inherent in methods of applying aloe vera to disposable articles.

Hence, improved designs for disposable absorbent articles and improved process for making the same are needed.

SUMMARY OF INVENTION

It is, therefore, an object of the present invention to provide a disposable absorbent article with improved rash prevention and reduction properties and comprising aloe vera.

An additional object of the present invention is to provide a disposable article comprising aloe vera which alleviates spoilage concerns.

Yet another object of the present invention is to provide a disposable absorbent article with improved comfort and reduced friction between the wearer's skin and the article.

Another object of the present invention is to provide a simple, improved method of manufacturing an absorbent article having improved rash prevention properties.

A further object of the present invention is to provide an improved method of manufacturing an absorbent article having an effective solution of aloe vera.

Another object of the present invention is to provide an improved method of manufacturing articles comprising aloe vera which alleviates spoilage concerns.

An additional object of the present invention is to provide a simple improved method of manufacturing an absorbent article having reduced friction between the wearer's skin and the article.

To achieve this invention's objects, there is provided in accordance with one aspect of the present invention a disposable absorbent article which comprises at least an inner layer in contact with the wearer's skin that comprises an effective amount of aloe vera to reduce rash and detrimental irritation of the wearer's body. For example, the effective amount of aloe vera should be at least about 0.0075 g of aloe vera per square meter of the inner layer. Preferably, the aloe vera is present in the range from about 0.0075 to 6 g/m$^2$, more preferably, from about 0.0075 to 0.33 g/m$^2$ and most preferably from about 0.025 to 0.22 g/m$^2$.

In accordance with another aspect of the present invention, there is provided an absorbent article comprising aloe vera in solution with a relatively waterless lubricant. For the purposes of the present invention, the term solution encompasses blends, combinations, admixtures, suspensions, homogeneous mixtures, heterogeneous mixtures and solutions. Preferably, the lubricant is petrolatum. Advantageously, the aloe vera used is an aloe vera-lubricant solution comprises about 0 to 200 g water to 1 g aloe vera solids. As the amount of aloe vera to water increases, the solution becomes more concentrated. According to a preferred embodiment, a concentrated aloe vera solution is used, and, in the most preferred solutions, an essentially water-free aloe vera is used. In this embodiment utilizing aloe vera in a lubricant solution, about 0.05–20 g of aloe vera is used with 1000 g of lubricant. More preferably, the amount of aloe vera is in the range of 1–3 g. Additionally, it is preferred if the solution is present in the range from about 0.75–7, and more preferably, 1.5–3, g of solution per square meter of inner layer.

To achieve another aspect of the present invention, there is provided a method of manufacturing an absorbent article comprising the steps of manufacturing an absorbent article and applying an effective concentration of aloe vera. For example, the applying step may incorporate at least about 0.0075 g of aloe vera per square meter of inner layer. Preferably, the aloe vera is applied by spraying. Advantageously, the aloe vera is sprayed onto the diaper at a pressure from about 5 to 50 psi. In this embodiment, it is preferred if the aloe vera/water solution has a ratio of at least 10:1, i.e., comprises at least 1 gram of aloe vera to 20 grams of water.

In accordance with yet another object of the present invention there is provided a method for manufacturing an absorbent article which alleviates aloe vera spoilage concerns comprising the steps of manufacturing an absorbent article, incorporating aloe vera into a relatively waterless lubricant solution, and applying the solution of aloe vera to areas of the absorbent article in contact with the wearer's skin. Preferably, the aloe vera solution comprises petrolatum. Advantageously, 0.075 to 7 g, and most advantageously, 1.5 to 3 g, of the preferred solution is applied per square meter of the inner layer of the absorbent article to which it is applied. The amount of aloe vera to lubricant is in the range from about 0.05 to 20 g aloe vera to 1000 g lubricant and, preferably from about 1 to 3 g aloe vera to 1000 g lubricant. Additionally, the aloe vera-lubricant solution is present in the range from about 0.75 to 7, and preferably from 1.5 to 3, g solution per square meter of the inner layer to which it is applied.

It is understood that references to aloe vera amounts in this description and the description and claims that follow refer to amounts of aloe vera solids.

Other objects, features and advantages of the present invention will become apparent from a review of the detailed description of the invention, including the appended claims that follow.

DETAILED DESCRIPTION OF INVENTION

Aloe vera is a naturally occurring substance produced by the aloe plant and is well known for its many applications. Aloe vera is available in a variety of forms, including powders and gels. For purposes of the present invention, the aloe vera may be selected from any of these forms. The only requirement is that the aloe vera be capable of application to the diaper as described herein. For example, aloe vera gel extracted from the fillet, or portion of the plant leaf encapsulated between the leaf's sheaths, is a water solution that can be easily applied to the diaper by a variety of steps to be described in more detail below.

Naturally occurring aloe vera comprises approximately 1 g of aloe vera solids per 200 g of water, and is generally referred to as 1:1 aloe vera. Commercially available aloe vera is often more concentrated and includes concentrations, such as 10:1, 40:1, and 200:1, which roughly correspond to concentrations of 1 g of aloe vera solids per 20 g of water, 1 g of aloe vera solids per 5 g of water, and waterless aloe vera solids. When applying aloe vera to absorbent articles, it is preferred that the addition of water be minimized, i.e., the aloe vera preferably be concentrated. Useful aloe vera products may be obtained, for example, from Aloecorp, Harlingen, Tex.

In addition to concentration, an additional consideration related to the present product concerns discoloration resulting from the inclusion of the aloe vera. Particularly, green coloration may occur. Preferably, discoloration concerns are substantially alleviated by filtration, for example, by charcoal bed filtration, to produce a neutral color at the application levels of the present invention. The filtration removes a mixture primarily consisting of anthroquinones.

Another consideration related to the present product concerns spoilage. Once aloe vera in a water based solution is exposed to the environment, the aloe vera begins to decompose and lose its effectiveness. Methods of alleviating spoilage concerns are addressed below.

As mentioned above, the unique rash-reducing product and method of making same according to the present invention are applicable to a variety of absorbent articles. These absorbent articles include disposable diapers, disposable training pants, feminine hygiene products and disposable adult incontinence articles. A disposable diaper will be discussed below for purposes of illustration, but not limitation.

Generally speaking, a disposable diaper has at least three operative layers. These layers include a liquid previous inner layer that contacts a baby's skin, an outer liquid impervious layer on the side of the inner layer opposite the child's body, and an absorbent layer positioned between the inner and outer layers. The diaper may also include upstanding leg cuffs that extend generally longitudinally along the diaper at least in the crotch area and leg elastics that generally are positioned about the leg openings. The materials of construction, methods of construction and functionality of these various diaper structures are well-known to those skilled in the art.

For purposes of the present invention, only the diaper structures in immediate contact with the baby's skin will be discussed in detail. These structures include the inner layer, leg elastics and leg cuffs. These structures form a cup area about the baby's upper thigh and crotch area to retain urinary and fecal discharge. As mentioned, the inner layer is liquid previous and generally constructed from a natural or woven or non-woven synthetic fabric which allows urine and other liquid to pass through the layer away from the baby's skin and into the absorbent layer. The leg elastics generally comprise elastic materials incorporated longitudinally along the lateral edges of the diaper. The leg elastics draw the edges of the diaper snugly about the baby's upper thighs. The upstanding leg cuffs, which may be laterally inside or outside the leg elastics, form a dam to assist is preventing lateral seepage from the diaper. The inclusion of cuffs, leg elastics or both is optional and not limiting to the scope of the present invention.

One of the objectives of the present invention is the inclusion of an effective amount of aloe vera to absorbent articles to effectively reduce the detrimental irritation and rash often associated with prolonged exposure of the wearer's body, particularly the genitals and buttocks to urine and other discharged liquids, or areas of the skin exposed to relatively high pressure areas of the diaper.

As discussed above, naturally occurring aloe vera gel has a concentration of approximately 1 g aloe vera solids to 200 g water. If applied to the diaper in this relatively dilute concentration, it has been found that the excessive water in the solution tends to wash away the surfactant that is often applied to the inner layer of the diaper to enhance permeability. Accordingly, in a preferred embodiment of the present invention, the aloe vera solution is concentrated. In the embodiment of the present invention in which aloe vera is used without a lubricant, aloe vera/water solutions having ratios of at least about 10:1, i.e., at least 1 g of aloe to 20 g of water, are preferred, and ratios of about 10:1–20:1 are particularly preferred. In the embodiment of the present invention in which aloe vera is combined with a lubricant and applied to the absorbent article, highly concentrated aloe vera is preferred and essentially water-free aloe vera is particularly preferred.

In addition to aloe vera concentrations, the present invention is also concerned with the effective amounts of aloe vera to include on the surface of the absorbent article that will contact the wearer. For example, in the embodiment in which aloe vera is used without lubricant, effective amounts of aloe vera for treating diaper rash generally exceed about 0.0075 g of aloe vera/$m^2$ and preferably range from about 0.0075 to 6 g of aloe vera solids/$m^2$. Particularly preferred are amounts from about 0.0075 to 0.33 g of aloe vera/$m^2$, for example, 0.025 to 0.22 g of aloe vera per $m^2$. It is to be understood that, for purposes of this disclosure, the square meter measure refers to the area of the inner layer of the absorbent article.

As previously noted, an additional aloe vera processing concern is spoilage. The spoilage rate can be reduced by a variety of compositions. For example, antioxidants and other preservatives can be added to the solution. Suggested preservatives include sodium benzoate and potassium sorbate. In addition, citric and lactic acids may be included to control pH and inhibit bacterial growth. Also, the solution, once opened, can be maintained in refrigerated containers. Alternatively or in addition to the above measures, the solution can be provided in smaller containers to minimize exposure times.

A particularly preferred means of controlling spoilage is incorporating aloe vera, and particularly a highly concentrated aloe vera, into a relatively waterless solution. For purposes of the present invention, the term solution encompasses blends, combinations, admixtures, suspensions, homogeneous mixtures, heterogeneous mixtures and solutions. Preferably, the other constituent of the solution is a lubricant. Most preferred, the lubricant is petrolatum. In this embodiment in which aloe vera is used in combination with a lubricant, particularly preferred solutions comprise from about 0.05 to 20 g of aloe vera per 1000 g of lubricant. Particularly preferred are concentrations of aloe vera from about 1 to 3 g per 1000 g of lubricant.

The use of the relatively waterless lubricant provides additional benefits. First, the use of a waterless composition reduces the likelihood that the surfactant will be washed away. Second, the aloe vera lubricant composition provides a protective layer between the skin and absorbent article, which reduces irritation caused by friction between the wearer's skin and high pressure areas of the diaper. In order to effectuate these advantages, the article preferably comprises from about 0.75 to 7 g of an aloe vera-lubricant solution/$m^2$. Most preferred, the article comprises from about 1.5 to 3 g/$m^2$ of an aloe vera-lubricant solution.

Another aspect of the present invention provides an improved method for applying an effective concentration of aloe vera to a disposable absorbent article. The aloe vera solution can be applied by a variety of processes. A particularly preferred process involves spraying the aloe vera solution onto the top surface of the inner layer of the diaper. As discussed above, effective amounts of aloe vera (when not used with a lubricant) for treating diaper rash generally equal or exceed 0.0075 g of aloe vera solids per $m^2$. Preferably, the aloe vera is present in an amount from about 0.0075 to 6, more preferably 0.0075–33, and most preferably, 0.025–0.22, g per square meter of inner layer. Another method is to mix aloe vera with surfactant solutions which may be applied to the nonwoven diaper topsheet.

The aloe vera can be applied continuously along the top surface of the inner layer or may be targeted to specific areas. It is particularly preferred to focus the higher concentrations of aloe vera in the areas of the diaper that experience high pressure contact with the baby, such as the crotch area, the leg elastics and the leg cuffs, and lesser concentrations in the areas of the diaper corresponding to the waist areas and other areas that do not experience substantial contact and exposure to the wearer. For example, concentrations from about 0.1 to 0.33 g of aloe vera solid per square meter may be applied to the leg cuffs, while concentrations of 0.01 to 0.03 g of efficacious solids may be applied to the topsheet.

Particularly preferred is intermittently spraying the solution to the targeted areas of the diaper. According to this preferred embodiment, a spray device, and particularly the spray nozzle thereof, is positioned along the manufacturing line in operative proximity to the newly manufactured diaper. For illustrative purposes, it is assumed that the targeted area is the crotch area of the diaper. Generally speaking, diapers are positioned on the conveyor line with the longitudinal axis generally parallel to the direction of travel. As a result the leading section of the diaper correspond to either the front or back waist section. As the leading waist section of the diaper passes by the spray nozzle, the nozzle remains closed. However, as the crotch area passes by the spray nozzle, the spray nozzle is operatively opened to introduce the aloe vera solution in the form of an atomized spray. Once the crotch area of the diaper moves beyond the effective spray area, the spray nozzle is closed and the trailing waist area of the diaper and the opposite waist area of the next succeeding diaper pass by the spray without receiving solution. The spray is again opened as the crotch area of the next succeeding diaper passes by the spray device. This process is repeated to assure that the aloe vera solution is concentrated in the area of the crotch where it will have the greatest effect in treating or preventing diaper rash.

Of course, the intermittent spraying may be programmed to apply the aloe vera solution to any defined area of the diaper, including the entirety of the diaper. This flexibility in coverage area is also true for the other methods of application to be discussed below. Furthermore, the application processing can be programmed to apply different levels of the aloe vera solution to different areas of the diaper. For example, higher concentrations can be applied to the crotch area, the leg elastics and leg cuffs and lower concentrations can be applied to the front and back waist areas since the latter areas are points of lower friction contact. Preferably, the aloe vera solution is sprayed onto the diaper at a pressure of from about 5 to 50 psi.

In addition to spraying, the aloe vera solution may be applied by a variety of rollers, including print-type rollers and engraved rollers. The common characteristic among these means of application is that each has the capability to apply the aloe vera solution to the top surface of the inner diaper layer and, preferably, to targeted areas of the diaper and in varying concentrations, as discussed above.

A water based aloe vera solution is tacky in its wet form and detrimentally affects the operability of the various diaper manufacturing machines if it contacts the machines while wet. Likewise, a waterless aloe vera solution is slippery and may also detrimentally affect the operability of the various diaper manufacturing machines. Accordingly, the aloe vera solution is preferably applied to the diaper after all contact between diaper and manufacturing machines is complete. A preferred application point is immediately after the completed diaper undergoes a folding step, generally referred to as a C-fold. The folding step is the last processing step that requires machine intervention against the top surface of the inner layer. The folding step is normally followed by packaging of the diaper. Even if the packaging is automatically performed, the machine does not contact the inner layer of the diaper, the aloe vera coated inner surface being folded onto itself and thus not exposed to the machine. The applied aloe vera solution does not require a special drying step.

As discussed above, aloe vera in water based solutions is prone to spoilage. In a preferred embodiment, spoilage concerns are alleviated by placing the aloe vera in a relatively waterless lubricant. Preferably, the lubricant is petrolatum. Most preferred, the solution comprises from about 0.05 to 20 g of aloe vera/1000 g of petrolatum. Preferably, the aloe vera and lubricant are mixed in a relatively uniform solution. The solution may then be applied in the methods discussed above. The solution is preferably applied in an amount from about 0.75 to 7, and more preferably from about 1.5 to 3, g solution/m$^2$.

While the invention has been disclosed with reference to certain described embodiments, numerous changes, alterations, and modifications of the described embodiments are possible without departing from the spirit and scope of the invention, as defined in the appended claims.

What is claimed is:

1. An absorbent article, comprising at least an inner layer that includes a solution for treating skin affected by diaper rash, said solution incorporating an amount of aloe vera as a primary ingredient in said solution for treating skin, wherein said amount of aloe vera is at least about 0.0075 g of aloe vera/m$^2$ of said inner layer.

2. The absorbent article as claimed in claim 1, wherein said inner layer includes from about 0.0075 to 6 g of said aloe vera/m$^2$ of said inner layer.

3. The absorbent article as claimed in claim 1, wherein said inner layer includes from about 0.0075 to 0.33 g of said aloe vera/m$^2$ of said inner layer.

4. The absorbent article as claimed in claim 1, wherein said inner layer includes from about 0.025 to 0.22 g of said aloe vera/m$^2$ of said inner layer.

5. The absorbent article as claimed in claim 1 further comprising a lubricant.

6. The absorbent article as claimed in claim 5, wherein said aloe vera is in a relatively waterless solution with said lubricant.

7. The absorbent article of claim 6, wherein said aloe vera is in a concentration from about 0.05 to 20 g per 1000 g of said lubricant.

8. The absorbent article of claim 6, wherein said aloe vera is in a concentration from about 1 to 3 g per 1000 g of said lubricant.

9. The absorbent article of claim 8, wherein said lubricant is petrolatum.

10. The absorbent article of claim 6, wherein said inner layer comprises from about 0.75–7 g said aloe vera-lubricant solution/m$^2$ of said inner layer.

11. The absorbent article of claim 6, wherein said inner layer comprises from about 1.5–3 g said aloe vera-lubricant solution/m$^2$ of said inner layer.

12. The absorbent article of claim 5, wherein said lubricant is petrolatum.

13. The absorbent article of claim 1, wherein said solution consists essentially of an aloe vera solids and water solution.

14. The absorbent article of claim 1, wherein said solution consists essentially of aloe vera solids and a lubricant.

15. The absorbent article of claim 14, wherein said lubricant is petrolatum.

16. The absorbent article of claim 15, wherein said aloe vera solids is in a concentration from about 1 to 3 g per 1000 g of petrolatum.

17. An absorbent article, comprising at least an inner layer that includes a solution for treating skin affected by diaper rash, said solution comprising aloe vera as a primary ingredient and a lubricant.

18. The absorbent article of claim 17, wherein said aloe vera is in a concentration from about 0.05 to 20 g per 1000 g of said lubricant.

19. The absorbent article of claim 17, wherein said aloe vera is in a concentration from about 1 to 3 g per 1000 g of said lubricant.

20. The absorbent article of claim 19, wherein said lubricant is petrolatum.

21. The absorbent article of claim 17, wherein said inner layer includes an amount of said solution from about 0.75 to 7 g/m$^2$ of said inner layer.

22. The absorbent article of claim 17, wherein said inner layer includes an amount of said solution from about 1.5 to 3 g/m$^2$ of said inner layer.

23. The absorbent article as claimed in claim 17, further comprising at least a pair of leg cuffs, wherein said inner layer includes from about 0.1 to 0.33 g of aloe vera/m$^2$ of said inner layer and each of said leg cuffs includes from about 0.01 to 0.03 g of aloe vera/m$^2$ of said inner layer.

24. The absorbent article as claimed in claim 17, wherein said aloe vera is an aqueous aloe vera having a concentration from about 0 to 200 g water per 1 g aloe vera solids.

25. A method for manufacturing an absorbent article, comprising the steps of:
    forming the absorbent article to include an inner layer having a top surface and a bottom surface; and
    applying a solution comprising aloe vera, as a primary ingredient for treating skin affected by diaper rash, to said top surface of said inner layer, wherein said applying step provides at least about 0.0075 g of aloe vera/m$^2$ of said inner layer.

26. The method as claimed in claim 25, wherein said applying step provides from about 0.0075 to 6 g aloe vera/m$^2$ of said inner layer.

27. The method as claimed in claim 25, wherein said aloe vera is sprayed onto said top surface of said inner layer.

28. The method as claimed in claim 27, wherein said aloe vera is intermittently sprayed onto said top surface.

29. The method as claimed in claim 25, wherein said aloe vera is sprayed onto said top surface at a pressure from about 5 to 50 psi.

30. The method as claimed in claim 25, wherein said aloe vera is rolled onto said top surface.

31. The method as claimed in claim 25, wherein said aloe vera is applied to the areas of said top surface that contact the skin of the wearer.

32. The method of claim 25, wherein said solution further comprises a surfactant.

33. The method as claimed in claim 25, wherein said applying step is performed subsequent to all steps which require contact of said top surface of said inner layer with machine parts.

34. The method as claimed in claim 25, wherein said aloe vera solution has a concentration by weight of from about 0 to 200 water to 1 g aloe vera solids.

35. The method as claimed in claim 25, wherein said aloe vera solution has a concentration by weight of from about 20 to 100 g of said aloe vera to 200 g water.

36. The method as claimed in claim 25, wherein said aloe vera is incorporated into a relatively waterless solution.

37. The method as claimed in claim 25, wherein said solution further comprises a lubricant.

38. The method as claimed in claim 37, wherein said aloe vera solution comprises about 0.05 to 20 of aloe vera per 1000 g of lubricant.

39. The method as claimed in claim 38, wherein said solution consists essentially of said aloe vera and said lubricant, and wherein said lubricant is petrolatum.

40. The method as claimed in claim 37, wherein said lubricant is petrolatum.

41. The method as claimed in claim 37, wherein said applying step provides from about 0.75 to 7 $g/m^2$ of said solution/$m^2$ of said inner layer.

42. The method as claimed in claim 25, wherein said aloe vera is concentrated aloe vera.

43. The method of claim 25, comprising the further step of applying a lubricant.

* * * * *